United States Patent
Zhong et al.

(10) Patent No.: US 10,451,564 B2
(45) Date of Patent: Oct. 22, 2019

(54) EMPIRICAL DETECTION OF LENS ABERRATION FOR DIFFRACTION-LIMITED OPTICAL SYSTEM

(71) Applicant: Applied Materials, Inc., Santa Clara, CA (US)

(72) Inventors: Qin Zhong, Santa Clara, CA (US); Antoine P. Manens, Saratoga, CA (US); Hwan J. Jeong, Los Altos, CA (US)

(73) Assignee: APPLIED MATERIALS, INC., Santa Clara ( * ) Notice: Subject to any disclaimer, the term of this patent is extended or adjusted under 35 U.S.C. 154(b) by 37 days.

(21) Appl. No.: 15/962,981

(22) Filed: Apr. 25, 2018

(65) Prior Publication Data

US 2019/0128825 A1 May 2, 2019

Related U.S. Application Data

(60) Provisional application No. 62/578,217, filed on Oct. 27, 2017.

(51) Int. Cl.
*G01N 21/958* (2006.01)
*G02B 26/08* (2006.01)
(Continued)

(52) U.S. Cl.
CPC ....... *G01N 21/958* (2013.01); *G01M 11/0278* (2013.01); *G02B 26/0833* (2013.01);
(Continued)

(58) Field of Classification Search
CPC ........ G01N 21/958; G01N 2021/9583; G01M 11/0278; G02B 26/0833; G03F 7/70025;
(Continued)

(56) References Cited

U.S. PATENT DOCUMENTS

2003/0098970 A1  5/2003  Chen
2004/0010385 A1  1/2004  Fukuhara et al.
(Continued)

FOREIGN PATENT DOCUMENTS

KR   20130034521 A   4/2013

OTHER PUBLICATIONS

PCT International Search Report/Written Opinion dated Dec. 7, 2018 for Application No. PCT/US2018/047836.

*Primary Examiner* — Jamil Ahmed
(74) *Attorney, Agent, or Firm* — Patterson + Sheridan LLP (57) ABSTRACT

A method for qualitatively detecting aberration and determine aberration types in a photolithography system is disclosed. The method includes using a digital micromirror device (DMD) pattern to project an optical signal on a reflective substrate, acquiring a return optical signal reflected from the substrate at different focus heights (ranging from above to below best focus), forming a through focus curve based off of the return optical signal at various focus heights, comparing the through focus curve to a predetermined curve—the predetermined curve being a function of focus, and determining if a lens aberration is present. By using the existing hardware of the photolithography system to determine if a lens aberration exists, costs are maintained at a minimum and the DMD pattern creates a through focus curve (TFC) image in less than five minutes allowing for quick correction.

20 Claims, 11 Drawing Sheets

(51) Int. Cl.
*G01M 11/02* (2006.01)
*G03F 7/20* (2006.01)
*G03F 9/00* (2006.01)

(52) U.S. Cl.
CPC .......... *G03F 7/706* (2013.01); *G03F 7/70025* (2013.01); *G03F 7/70291* (2013.01); *G03F 7/70316* (2013.01); *G03F 9/7026* (2013.01); *G01N 2021/9583* (2013.01)

(58) Field of Classification Search
CPC .. G03F 7/70291; G03F 7/70316; G03F 7/706; G03F 9/7026
See application file for complete search history.

(56) References Cited

U.S. PATENT DOCUMENTS

| | | |
|---|---|---|
| 2004/0174506 A1 | 9/2004 | Smith |
| 2009/0255911 A1 | 10/2009 | Krishnaswami et al. |
| 2009/0314751 A1 | 12/2009 | Manens et al. |
| 2009/0314752 A1 | 12/2009 | Manens et al. |
| 2010/0252543 A1 | 10/2010 | Manens et al. |
| 2010/0267318 A1 | 10/2010 | Duboust et al. |
| 2010/0314367 A1 | 12/2010 | Shamoun et al. |
| 2011/0033970 A1 | 2/2011 | Manens et al. |
| 2011/0139755 A1 | 6/2011 | Manens et al. |
| 2011/0139758 A1 | 6/2011 | Fan et al. |
| 2011/0198322 A1 | 8/2011 | Manens et al. |
| 2011/0242520 A1* | 10/2011 | Kosugi ................... G03F 7/706 355/77 |
| 2011/0253685 A1 | 10/2011 | Hsu et al. |
| 2018/0024448 A1 | 1/2018 | Tung et al. |

\* cited by examiner

EMPIRICAL DETECTION OF LENS ABERRATION FOR DIFFRACTION-LIMITED OPTICAL SYSTEM

CROSS-REFERENCE TO RELATED APPLICATIONS

This application claims benefit of U.S. Appl. No. 62/578,217, filed Oct. 27, 2017, which is herein incorporated by reference.

BACKGROUND

Field

Implementations of the present disclosure generally relate to systems and methods for processing one or more substrates, and more specifically to apparatuses, systems and methods for performing photolithography processes.

Description of the Related Art

Photolithography is widely used in the manufacturing of semiconductor devices and display devices, such as liquid crystal displays (LCDs). Large area substrates are often utilized in the manufacture of LCDs. LCDs, or flat panels, are commonly used for active matrix displays, such as computers, touch panel devices, personal digital assistants (PDAs), cell phones, television monitors, and the like. Generally, flat panels may include a layer of liquid crystal material forming pixels sandwiched between two plates. When power from the power supply is applied across the liquid crystal material, an amount of light passing through the liquid crystal material may be controlled at pixel locations enabling images to be generated.

Microlithography techniques are generally employed to create electrical features incorporated as part of the liquid crystal material layer forming the pixels. According to this technique, a light-sensitive photoresist is typically applied to at least one surface of a substrate. Then, a pattern generator exposes selected areas of the light-sensitive photoresist as part of a pattern with light to cause chemical changes to the photoresist in the selective areas to prepare these selective areas for subsequent material removal and/or material addition processes to create the electrical features. During processing, the lens focus is a critical parameter and can affect the circuit pattern quality and accuracy in a non-trivial way. Focus generally deals with clarity with which an optical subsystem of the lithography system renders an image. Changes in focus may cause changes in the resist profile and the shape of the circuit printed in the photoresist. Lens aberration is another critical process parameter which could result in degradation of the quality of the circuit printed in the photoresist, such as shift of focus, pattern distortion, and critical dimension inconsistency. Lens aberration could be determined by inspecting the quality of printed pattern; however, this method is time consuming and unreliable.

Therefore, an improved photolithography system for determining on tool aberration measurement is needed for a photolithography tool.

SUMMARY

Implementations of the present disclosure generally relate to methods for performing photolithography processes. In one implementation, the method includes using a specific digital micromirror device (DMD) pattern to project an optical image on a reflective substrate, acquiring a picture of returned optical image from the substrate using a camera, forming a through focus curve based on processing the return optical image, comparing the through focus curve to a predetermined curve—the predetermined curve being a function of focus, and determining if a lens aberration is present.

In another implementation, a method for determining focus is disclosed. The method includes using a first DMD pattern to project a first optical image on a reflective substrate, acquiring a first return optical image from the substrate, forming a first through focus curve based off of the first return optical image, comparing the first through focus curve to a predetermined curve—the predetermined curve being a function of focus, determining if a lens aberration is present, using a second DMD patterns to project a second optical signal on the substrate, acquiring a second return optical signal from the substrate, and using the second return optical signal to determine a lens aberration type.

In yet another implementation, a method for determining focus is disclosed. The method includes using a first DMD pattern to project a first optical on a reflective substrate, acquiring a first return optical image from the substrate, forming a first through focus curve based off of the first return optical image; using a second DMD pattern to project a second optical image on the reflective substrate, acquiring a second return optical image from the substrate, forming a second through focus curve based off of the second return optical image. Comparing the first through focus curve to the second through focus curve and determining a specific lens aberration type.

BRIEF DESCRIPTION OF THE DRAWINGS

So that the manner in which the above recited features of the present disclosure can be understood in detail, a more particular description of the disclosure, briefly summarized above, may be had by reference to implementations, some of which are illustrated in the appended drawings. It is to be noted, however, that the appended drawings illustrate only typical implementations of this disclosure and are therefore not to be considered limiting of its scope, for the disclosure may admit to other equally effective implementations.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Implementations of the present disclosure relate to a method for qualitatively detecting aberrations in a photolithography system. The method includes using a digital micromirror device (DMD) to project an optical signal or pattern on a reflective substrate, acquiring a return optical signal from the substrate, forming a through focus curve (TFC) based off of the return optical signal, comparing the through focus curve to a predetermined curve—the predetermined curve being a function of focus height, and determining if a lens aberration is present. By using the existing hardware of the photolithography system to determine if a lens aberration exists, costs are maintained at a minimum, and total time collecting images for DMD pattern at different focus heights and forming a TFC based on collected images are less than five minutes, which allows for quick detection and diagnostics.

Figure 1A:
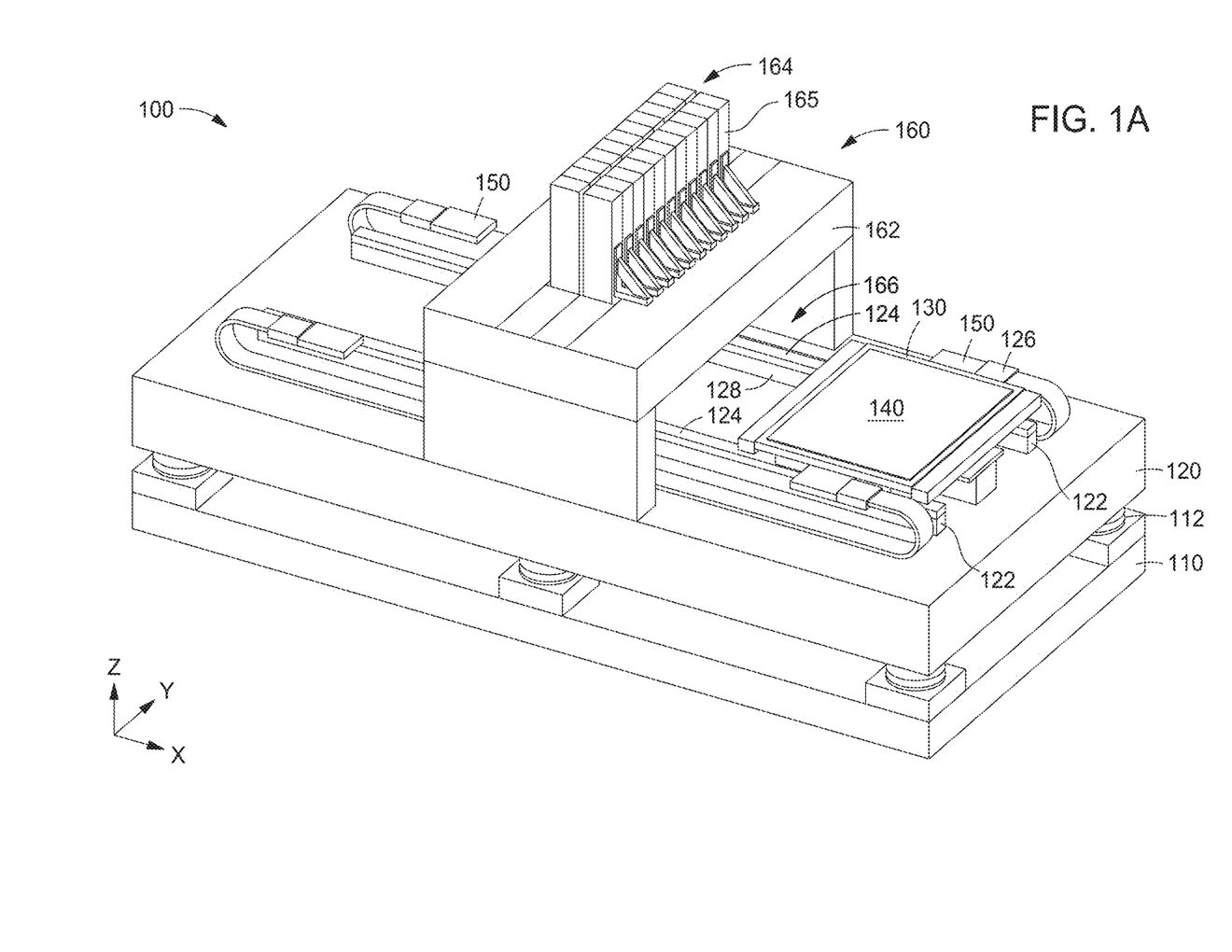
FIG. 1A is a perspective view of a photolithography system according to embodiments disclosed herein.

FIG. 1A is a perspective view of a photolithography system 100 according to embodiments disclosed herein. The photolithography system 100 includes a base frame 110, a slab 120, a stage 130, and a processing apparatus 160. The base frame 110 rests on the floor of a fabrication facility and supports the slab 120. Passive air isolators 112 are positioned between the base frame 110 and the slab 120. In one embodiment, the slab 120 is a monolithic piece of granite, and the stage 130 is disposed on the slab 120. A substrate 140 is supported by the stage 130. A plurality of holes (not shown) are formed in the stage 130 for allowing a plurality of lift pins (not shown) to extend therethrough. In some embodiments, the lift pins rise to an extended position to receive the substrate 140, such as from one or more transfer robots (not shown). The one or more transfer robots are used to load and unload a substrate 140 from the stage 130.

The substrate 140 comprises any suitable material, for example, quartz used as part of a flat panel display. In other embodiments, the substrate 140 is made of other materials. In some embodiments, the substrate 140 has a photoresist layer formed thereon. A photoresist is sensitive to radiation. A positive photoresist includes portions of the photoresist, which when exposed to radiation, will be respectively soluble to photoresist developer applied to the photoresist after the pattern is written into the photoresist. A negative photoresist includes portions of the photoresist, which when exposed to radiation, will be respectively insoluble to photoresist developer applied to the photoresist after the pattern is written into the photoresist. The chemical composition of the photoresist determines whether the photoresist will be a positive photoresist or negative photoresist. Examples of photoresists include, but are not limited to, at least one of diazonaphthoquinone, a phenol formaldehyde resin, poly (methyl methacrylate), poly(methyl glutarimide), and SU-8. In this manner, the pattern is created on a surface of the substrate 140 to form the electronic circuitry.

The photolithography system 100 includes a pair of supports 122 and a pair of tracks 124. The pair of supports 122 are disposed on the slab 120, and the slab 120 and the pair of supports 122 are a single piece of material. The pair of tracks 124 is supported by the pair of the supports 122, and the stage 130 moves along the tracks 124 in the X-direction. In one embodiment, the pair of tracks 124 is a pair of parallel magnetic channels. As shown, each track 124 of the pair of tracks 124 is linear. In other embodiments, one or more track 124 is non-linear. An encoder 126 is coupled to the stage 130 in order to provide location information to a controller (not shown).

The processing apparatus 160 includes a support 162 and a processing unit 164. The support 162 is disposed on the slab 120 and includes an opening 166 for the stage 130 to pass under the processing unit 164. The processing unit 164 is supported by the support 162. In one embodiment, the processing unit 164 is a pattern generator configured to expose a photoresist in a photolithography process. In some embodiments, the pattern generator is configured to perform a maskless lithography process. The processing unit 164 includes a plurality of image projection apparatus (shown in FIGS. 2A and 2B). In one embodiment, the processing unit 164 contains as many as 84 image projection apparatus. Each image projection apparatus is disposed in a case 165. The processing apparatus 160 is useful to perform maskless direct patterning.

During operation, the stage 130 moves in the X-direction from a loading position, as shown in FIG. 1, to a processing position. The processing position is one or more positions of the stage 130 as the stage 130 passes under the processing unit 164. During operation, the stage 130 is be lifted by a plurality of air bearings (not shown) and moves along the pair of tracks 124 from the loading position to the processing position. A plurality of vertical guide air bearings (not shown) are coupled to the stage 130 and positioned adjacent an inner wall 128 of each support 122 in order to stabilize the movement of the stage 130. The stage 130 also moves in the Y-direction by moving along a track 150 for processing and/or indexing the substrate 140. The stage 130 is capable of independent operation and can scan a substrate 140 in one direction and step in the other direction.

A metrology system measures the X and Y lateral position coordinates of each of the stage 130 in real time so that each of the plurality of image projection apparatus can accurately locate the patterns being written in a photoresist covered substrate. The metrology system also provides a real-time measurement of the angular position of each of the stage 130 about the vertical or Z-axis. The angular position measurement can be used to hold the angular position constant during scanning by means of a servo mechanism or it can be used to apply corrections to the positions of the patterns being written on the substrate 140 by the image projection apparatus 270, shown in FIGS. 2A and 2B. These techniques may be used in combination.

Figure 1B:
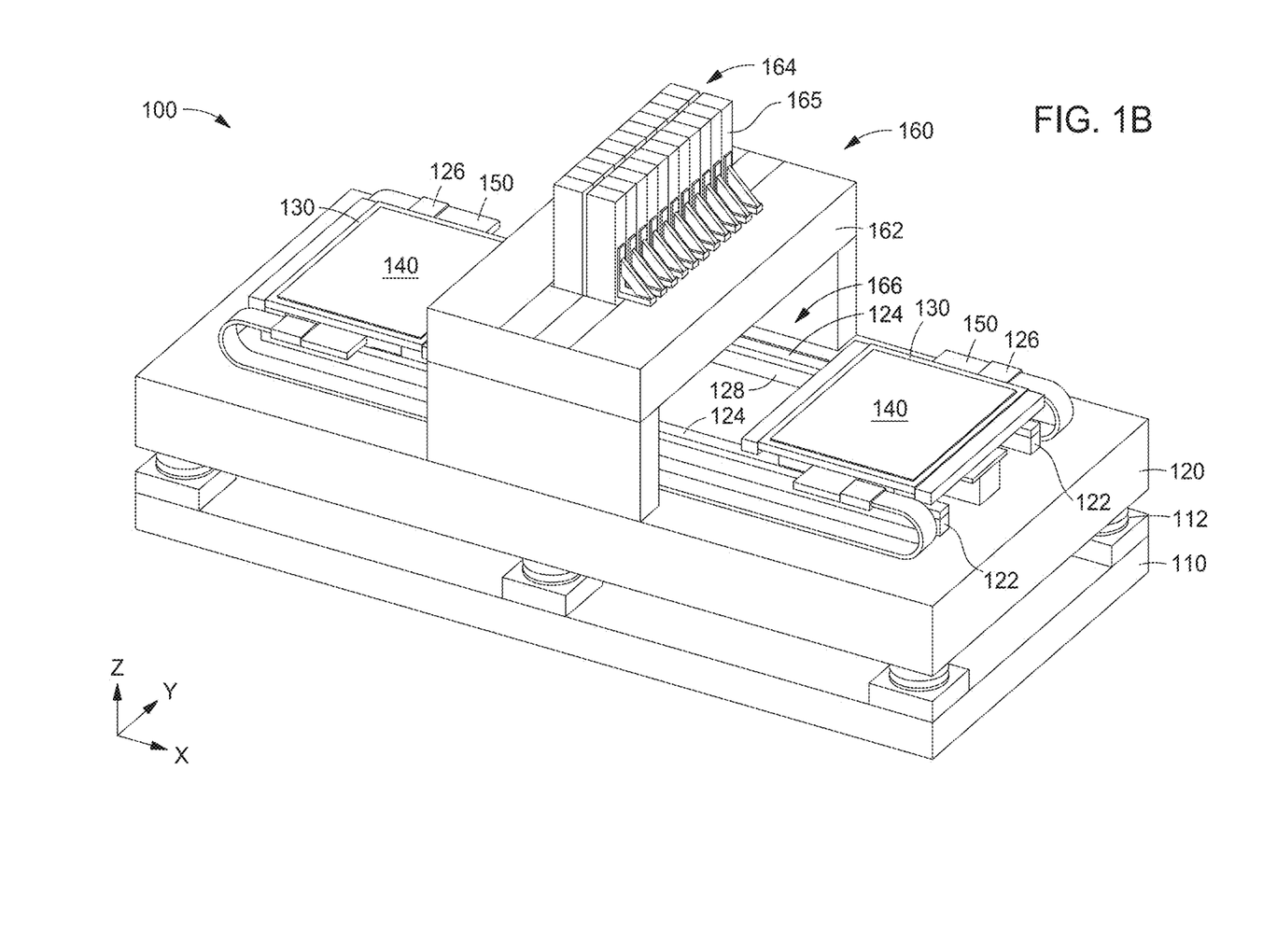
FIG. 1B is a perspective view of a photolithography system according to embodiments disclosed herein.

FIG. 1B is a perspective view of a photolithography system 200 according to embodiments disclosed herein. The photolithography system 200 is similar to the photolithography system 100; however, the photolithography system 200 includes two stages 130. Each of the two stages 130 is capable of independent operation and can scan a substrate 140 in one direction and step in the other direction. In some embodiments, when one of the two stages 130 is scanning a substrate 140, another of the two stages 130 is unloading an exposed substrate and loading the next substrate to be exposed.

While FIGS. 1A and 1B depict two embodiments of a photolithography system, other systems and configurations are also contemplated herein. For example, photolithography systems including any suitable number of stages are also contemplated.

Figure 2A:
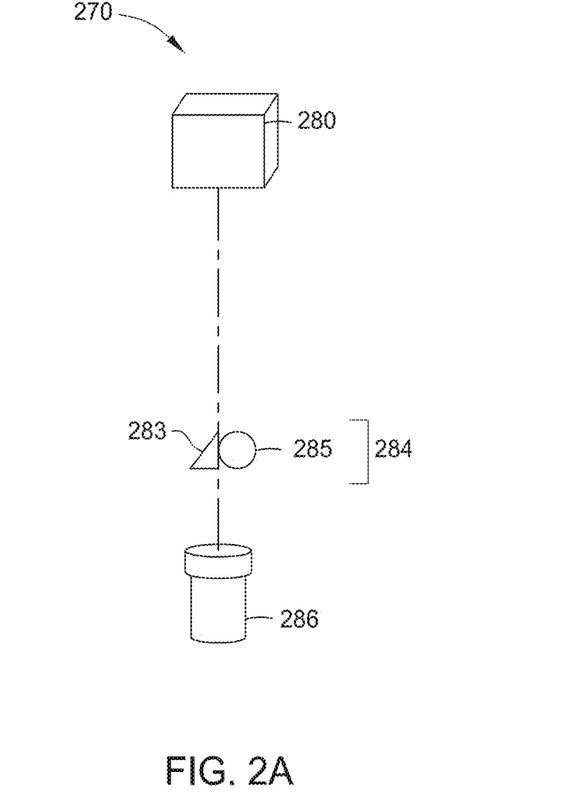
FIG. 2A is a perspective schematic view of an image projection apparatus according to embodiments disclosed herein.

FIG. 2A is a perspective schematic view of an image projection apparatus 270 according to one embodiment, which is useful for a photolithography system, such as system 100 or system 200. The image projection apparatus 270 includes one or more spatial light modulators 280, an alignment and inspection system 284 including a focus sensor 283 and a camera 285, and projection optics 286. The components of image projection apparatus vary depending on the spatial light modulator being used. Spatial light modulators include, but are not limited to, microLEDs, digital micromirror devices (DMDs) and liquid crystal displays (LCDs).

In operation, the spatial light modulator 280 is used to modulate one or more properties of the light, such as amplitude, phase, or polarization, which is projected through the image projection apparatus 270 and to a substrate, such as the substrate 140. The alignment and inspection system 284 is used for alignment and inspection of the components of the image projection apparatus 270. In one embodiment, the focus sensor 283 includes a plurality of lasers which are directed through the lens of the camera 285 and the back through the lens of the camera 285 an imaged onto sensors to detect whether the image projection apparatus 270 is in focus. The camera 285 is used to image the substrate, such as substrate 140, to ensure the alignment of the image projection apparatus 270 and photolithography system 100 or 200 is correct or within an predetermined tolerance. The projection optics 286, such as one or more lenses, is used to project the light onto the substrate, such as the substrate 140.

Figure 2B:
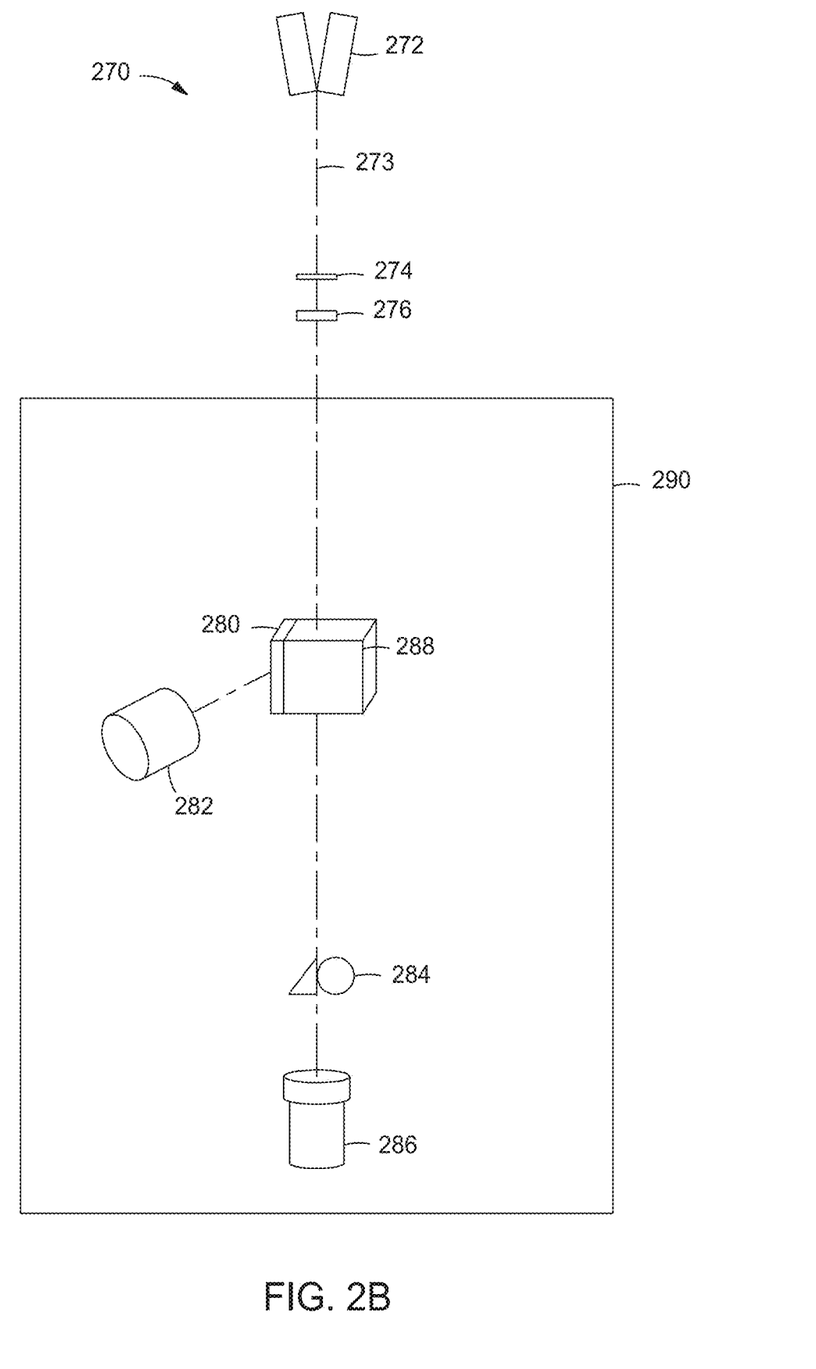
FIG. 2B is a perspective schematic view of an image projection apparatus according to embodiments disclosed herein.

FIG. 2B is an image project apparatus 281 according to embodiments described herein. In the embodiment shown in FIG. 2B, the image projection apparatus 281 uses one or more DMDs 289 as the spatial light modulator(s). The image projection apparatus 281 is part of an image projection system 290, which includes a light source 272, an aperture 274, a lens 276, a frustrated prism assembly 288, one or more DMDs 289 (one is shown), and a light dump 282, in addition to the alignment and inspection system 284 and the projection optics 286. The light source 272 is any suitable light source, such as a light emitting diode (LED) or a laser, capable of producing a light beam having predetermined wavelength. In one or more embodiments, the light beam has with a wavelength in a range from about 400 nm to about 750 nm. In other embodiments, the predetermined wavelength is in the blue or near ultraviolet (UV) range, such as less than 450 nm. For example, the light beam has a wavelength in a range from about 360 nm to about 410 nm. The frustrated prism assembly 288 includes a plurality of reflective surfaces. The projection optics 286 is, as an example, a 6× objective lens.

During operation of the image projection apparatus 281 shown in FIG. 2B, a light beam 273 having a predetermined wavelength, such as a wavelength in the blue range, is produced by the light source 272. The light beam 273 is reflected to the DMD 289 by the frustrated prism assembly 288. The DMD includes a plurality of mirrors, and the number of mirrors corresponds to the number of pixels to be projected. In one implementation, the DMD 289 includes 2,560×1,600 mirrors. The plurality of mirrors are individually controllable, and each mirror of the plurality of mirrors is at an "on" position or "off" position, based on the mask data provided to the DMD 289 by the controller (not shown). In one implementation, the combination of mirrors in "on" positions and "off" positions forms the desired pattern.

When the light beam 273 reaches the mirrors of the DMD 289, the mirrors that are at "on" position reflect the light beam 273, e.g., forming the plurality of write beams, to the projection optics 286. The projection optics 286 then projects the write beams to the surface of the substrate 140. The mirrors that are at "off" position reflect the light beam 273 to the light dump 282 instead of the surface of the substrate 140.

Figure 3:
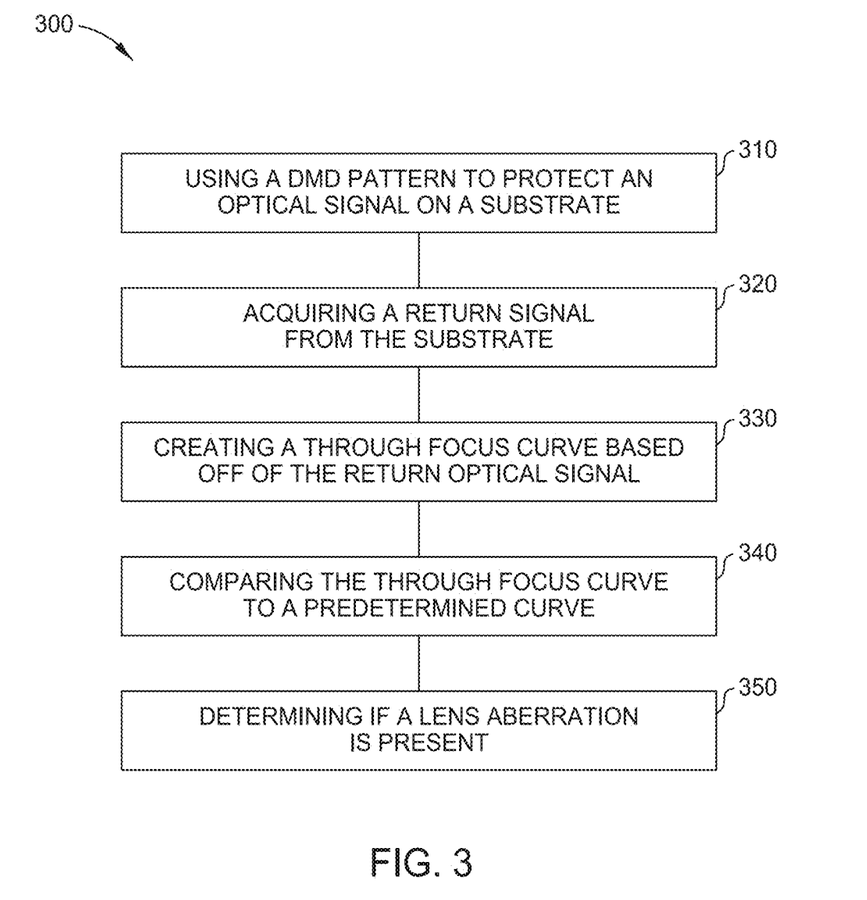
FIG. 3 is a flow chart of a method for detecting a lens aberration.

FIG. 3 is a flow chart that depicts a method 300 of detecting a lens aberration. At operation 310, a DMD is used to project an optical signal pattern to a target on a substrate. Specifically, a narrow light beam 273 is directed through one side of the pupil in the projection optics 286, through different DMD patterns.

Figure 4A:
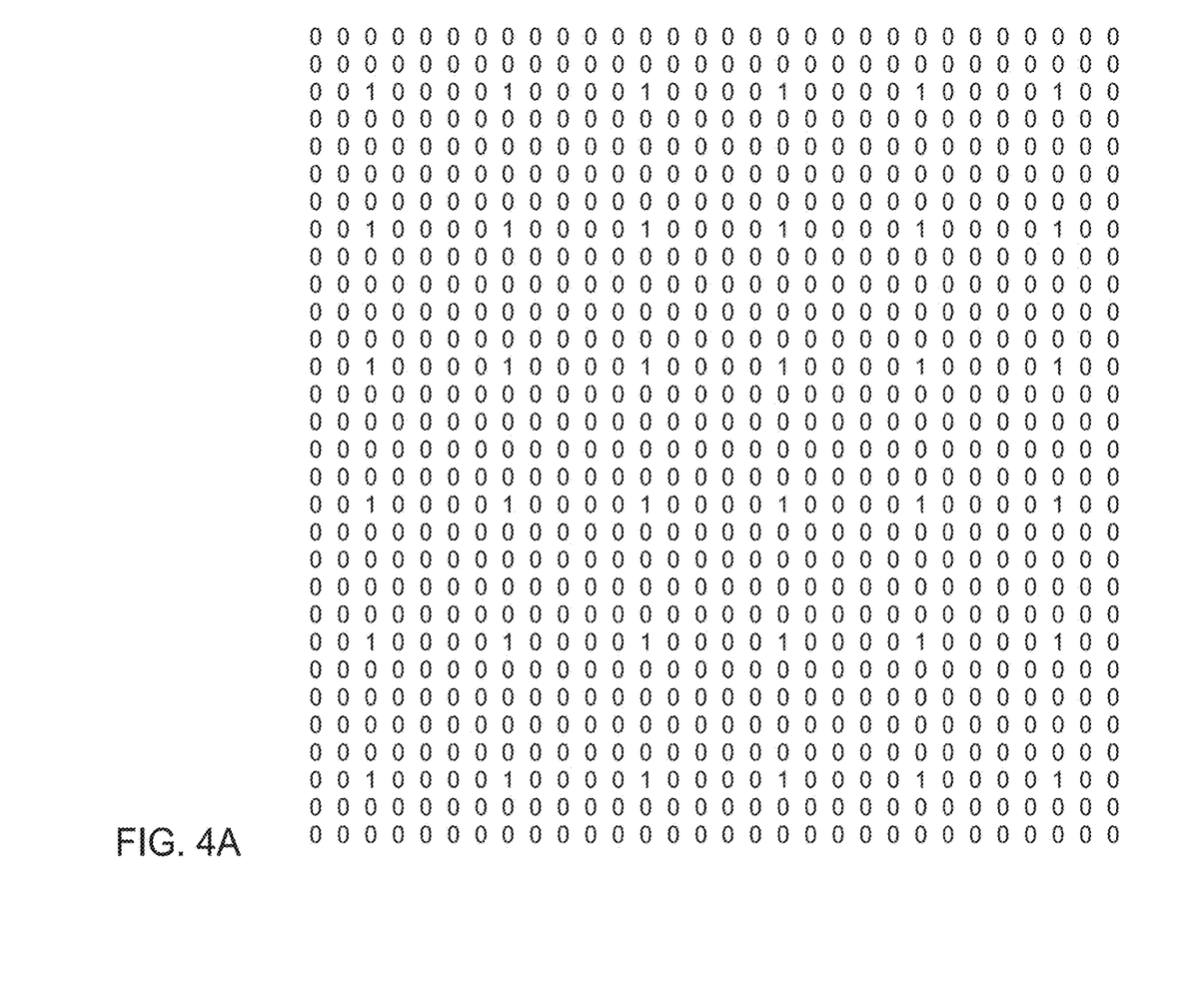
FIG. 4A is a schematic view of a Dots5×5 pattern according to embodiments disclosed herein.
Figure 4B:
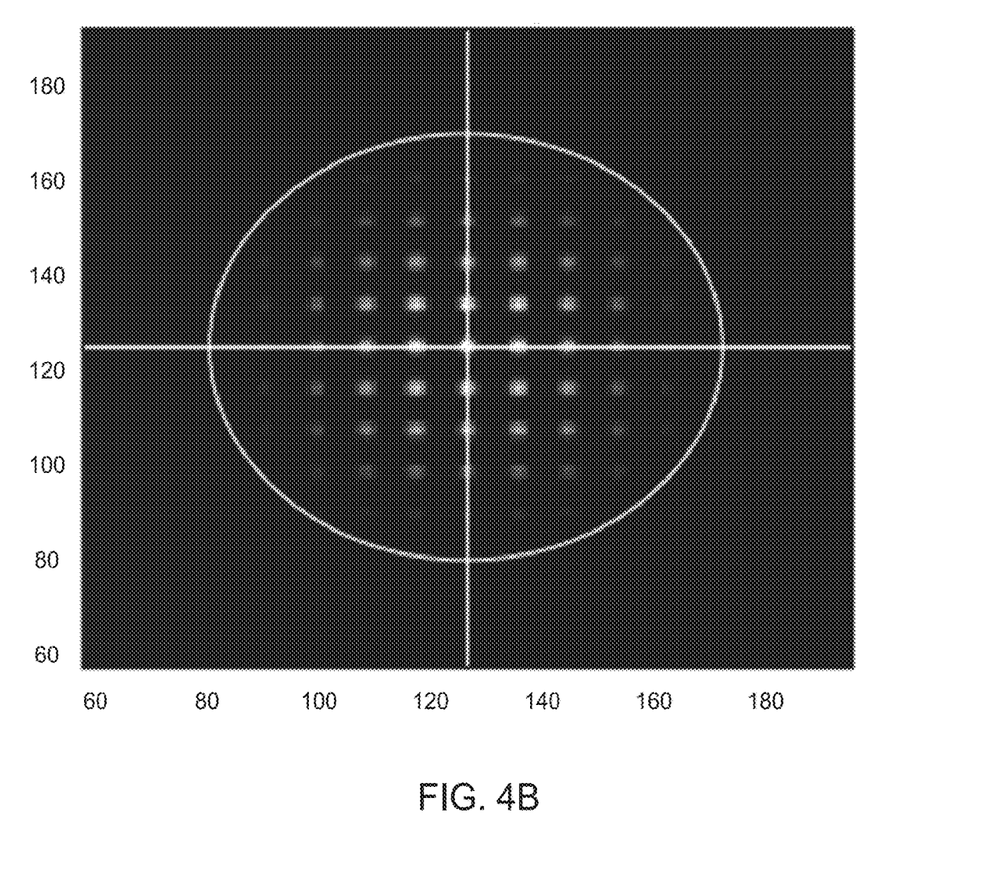
FIG. 4B is a schematic view of a Dots5×5 pupil image according to embodiments disclosed herein.

In one implementation, the DMD pattern is a Dots5×5 pattern image, as depicted in FIG. 4A. In another aspect, the optical image projected in the Dots5×5 pattern has a large pupil, as depicted in FIG. 4B, to capture larger area of optics on the substrate. In FIGS. 4A and 4B, the "1s" are indicative of the mirrors that are at the "on" position and the "0s" are indicative of the mirrors that are at "off" positions.

Figure 5A:
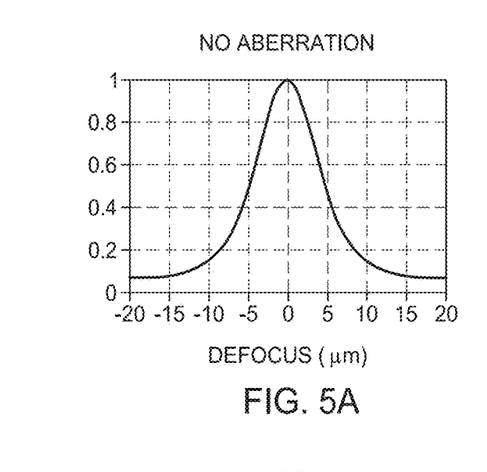
FIGS. 5A-5E are graphs of focus curves from Dots5×5 pattern focus curves according to embodiments disclosed herein.
Figure 5B:
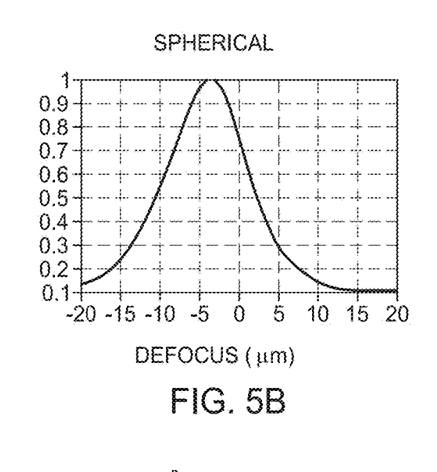
Figure 5C:
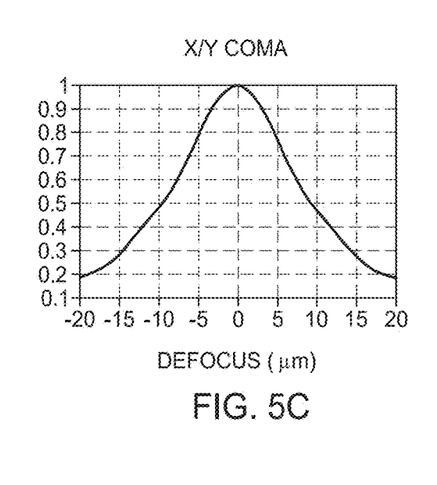
Figure 5D:
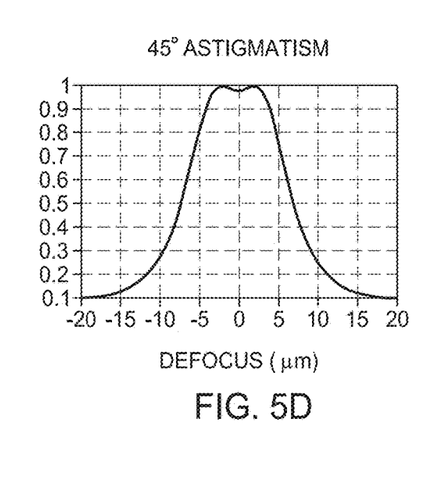
Figure 5E:
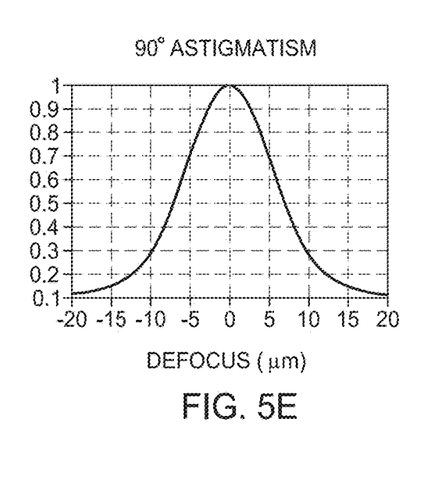

FIGS. 5A-5E are graphs of focus curves from Dots5×5 pattern focus curves. These focus curves include no aberration (FIG. 5A), spherical (FIG. 5B), X/Y coma (FIG. 5C), 45° astigmatism (FIG. 5D), and 90° astigmatism (FIG. 5E).

Figure 6A:
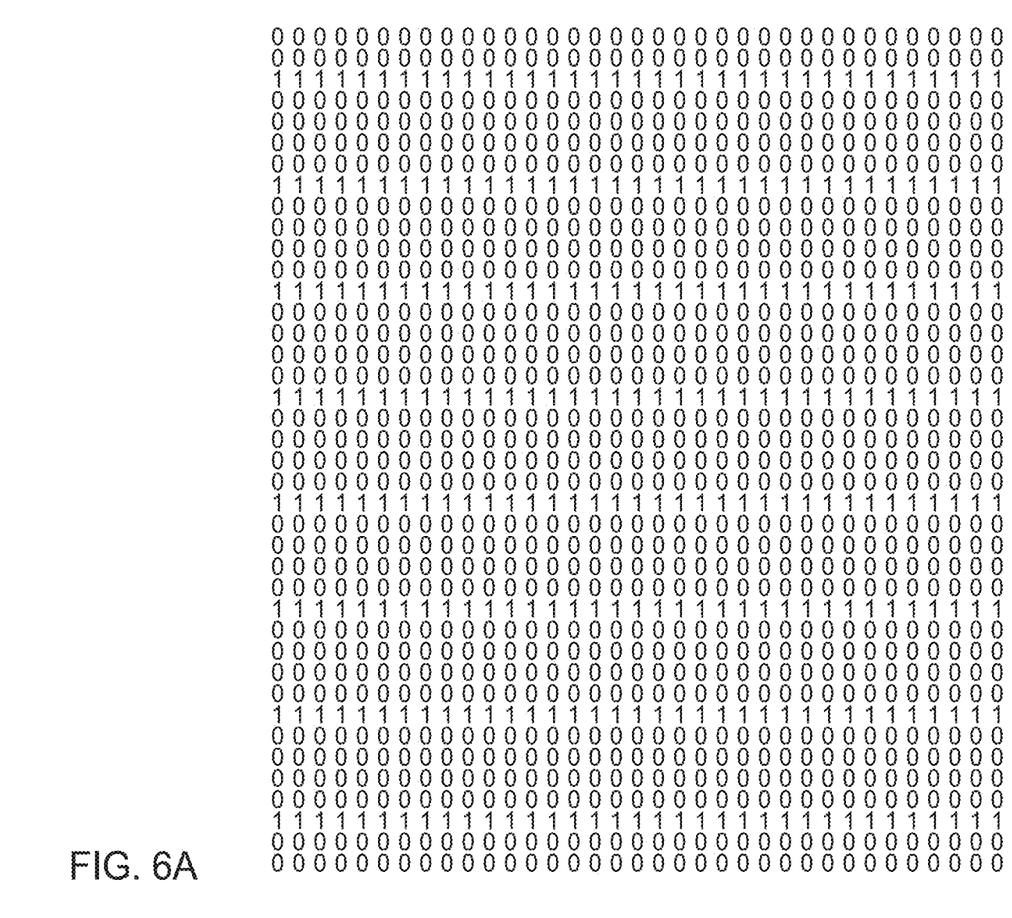
FIG. 6A is a schematic view of a horizontal stripes pattern according to embodiments disclosed herein.
Figure 6B:
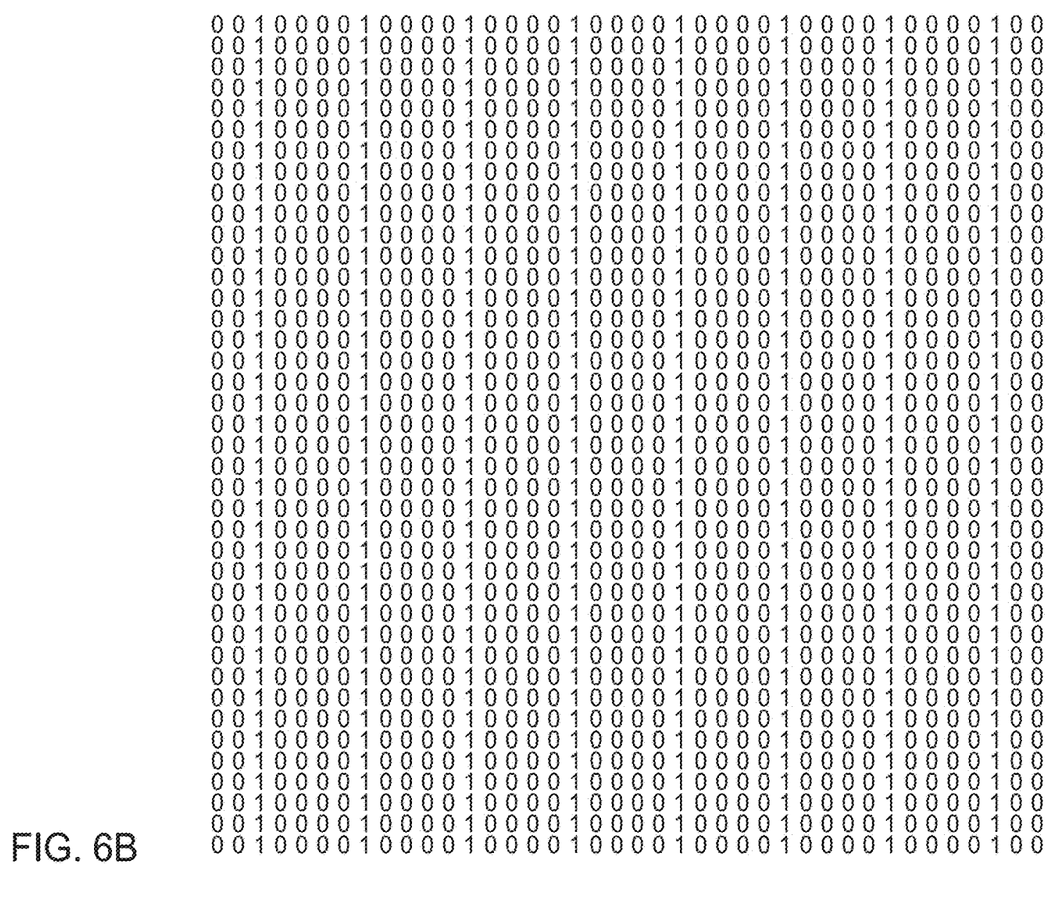
FIG. 6B is a schematic view of a vertical stripes pattern according to embodiments disclosed herein.
Figure 7A:
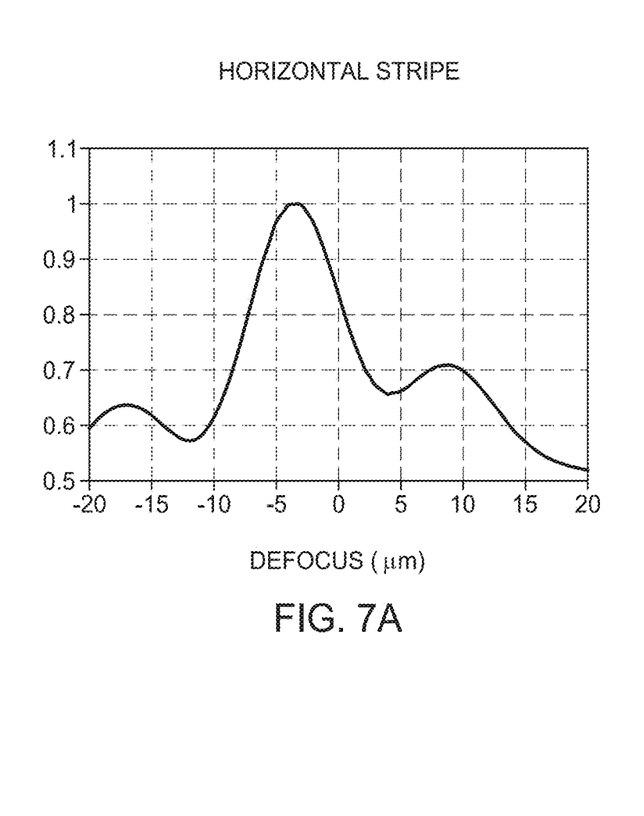
FIG. 7A is a graph of a horizontal stripes pattern focus curve according to embodiments disclosed herein.
Figure 7B:
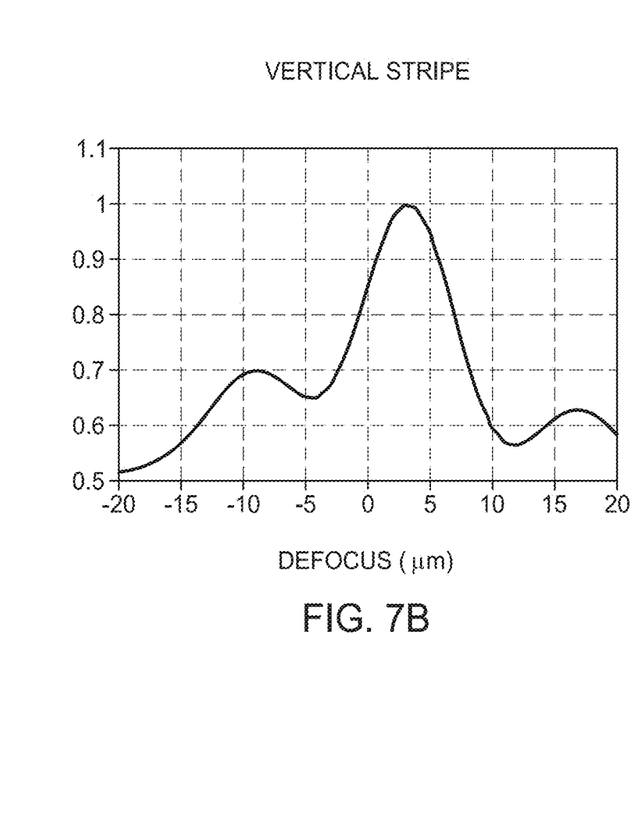
FIG. 7B is a graph of a vertical stripes pattern focus curve according to embodiments disclosed herein.

In another implementation, the DMD pattern is a horizontal stripes pattern, as depicted in FIG. 6A. In another implementation, the DMD pattern is a vertical stripes pattern, as depicted in FIG. 6B. In FIGS. 6A and 6B, the "1s" are indicative of the mirrors that are at the "on" position and the "0s" are indicative of the mirrors that are at "off" positions. Each of the horizontal and vertical patterns has a focus curve that depicts the impact of astigmatism, as shown in the graphs of the horizontal strip pattern (FIG. 7A) and the vertical strip pattern (FIG. 7B). In another implementation, the DMD pattern is a gray or 45° stripes pattern (not shown), such as a hybrid of the horizontal and vertical patterns.

In another implementation, a plurality of DMD patterns is used. For example, both the vertical stripes and horizontal stripes pattern may be used in combination. Different combinations of DMD patterns could be sensitive to specific aberration types. For example, the horizontal and vertical stripes patterns are more sensitive to astigmatism)(90° aberrations while 45° stripes patterns are more sensitive to 45° astigmatisms. More specifically, the horizontal stripes pattern are used to detect X-coma and the vertical stripes pattern are used to detect Y-coma. Also, the 45° stripes patterns can include a +45° stripes pattern and/or a −45° stripes pattern.

At operation 320 of the method 300, a return optical signal is acquired from the substrate. At operation 330, a through focus curve is created based off of the return optical signal. The light beam 273 strikes the substrate 140 at an oblique angel and is reflected back so that it traverses the opposite side of the pupil producing a through focus curve (TFC) image. An image projection detector or camera accurately measures the TFC shape, symmetry, width, and intensity of the return image to determine whether a lens aberration exists. In one implementation, a dark field single pass light beam is produced. In another implementation, a bright field double pass TFC light beam is produced. At operations 340 and 350, the TFC image is then compared to a predetermined curve to determine whether an aberration exists. The predetermined curve is a function of focus. In one implementation, the predetermined curve is the focus curve of a substrate without any aberrations. The Dots5×5 pattern has a large pupil image that produces a TFC curve showing signs of any local lens aberration. For example, changes in the Dots5×5 pattern can be correlated to a spherical lens aberration, a coma aberration, and an astigmatism aberration. An asymmetric change in the Dots5×5 pattern when compared to the predetermined curve is indicative of a spherical lens aberration. A broadened change in the Dots5×5 pattern when compared to the predetermined curve is indicative of a coma and astigmatism aberration. A change in the focus position of the substrate 140 can be used to bring the projection optics 286 back into good focus. The change is proportional to the amount of defocus and the direction of image motion determined by the type of aberration that exists.

By using the existing hardware of the photolithography system to determine if a lens aberration exists, costs are maintained at a minimum. Additionally, the DMD pattern creates a TFC image in less than five minutes allowing for quick correction, eliminating wasted printed substrates that have errors and are no longer usable products. Finally, by utilizing the various DMD patterns, not only is an aberration determined, the type of aberration is determined providing for meaningful lens correction.

While the foregoing is directed to implementations of the present disclosure, other and further implementations of the disclosure may be devised without departing from the basic scope thereof, and the scope thereof is determined by the claims that follow.

The invention claimed is:

1. A method of determining focus in a photolithography system, comprising:
   using a digital micromirror device (DMD) pattern to project an optical signal on a substrate;
   acquiring a return optical signal from the substrate;
   measuring one or more focus heights of the return optical signal;
   forming a through focus curve based off of the one or more focus heights of the return optical signal;
   comparing the through focus curve to a predetermined curve, wherein the predetermined curve is a function of focus; and
   determining if a lens aberration is present.

2. The method of claim 1, wherein the DMD pattern is a Dots5×5 pattern.

3. The method of claim 1, wherein the optical signal is a light beam.

4. The method of claim 3, wherein the light beam has a wavelength in a range from about 360 nm to about 410 nm.

5. The method of claim 3, wherein a combination of mirrors in on positions and off positions forms the DMD pattern.

6. The method of claim 1, wherein the return optical signal is a light beam created from the reflection and transformation of the first optical signal.

7. The method of claim 1, wherein the return optical signal is acquired by a camera.

8. A method of determining an aberration, comprising:
   using a first digital micromirror device (DMD) pattern to project a first optical signal on a substrate;
   acquiring a first return optical signal from the substrate;
   forming a first through focus curve based off of the first return optical signal;
   comparing the first through focus curve to a predetermined curve, wherein the predetermined curve is a function of focus;
   determining if a lens aberration is present;
   using a second DMD pattern to project a second optical signal on the substrate;
   acquiring a second return optical signal from the substrate;
   forming a second through focus curve based off of the second return optical signal;
   and
   comparing the first through focus curve to the second through focus curve to determine a lens aberration type.

9. The method of claim 8, wherein the first DMD pattern is a horizontal stripes.

10. The method of claim 8, wherein the optical signal is a light beam.

11. The method of claim 10, wherein the light beam has a wavelength in a range from about 360 nm to about 410 nm.

12. The method of claim 9, wherein the second DMD pattern is a vertical stripe pattern.

13. The method of claim 8, wherein the first DMD pattern is a Dots5×5 pattern.

14. The method of claim 13, wherein the second DMD pattern is a vertical stripe pattern.

15. A method of determining focus, the method comprising:
   using a first digital micromirror device (DMD) pattern to project a first optical signal on a substrate;
   acquiring a first return optical signal from the substrate;
   forming a first through focus curve based off of the first return optical signal;
   comparing the first through focus curve to a predetermined curve, wherein the predetermined curve is a function of focus;
   using a plurality of DMD patterns to project a second optical signal on the substrate;
   acquiring a second return optical signal from the substrate; and
   determining a lens aberration type.

16. The method of claim 15, further comprising:
   forming a second through focus curve based off of the second return optical signal; and
   comparing the second through focus curve to a predetermined curve to determine the lens aberration type.

17. The method of claim 15, wherein the plurality of DMD patterns comprises a horizontal stripe pattern and a vertical stripe pattern.

18. The method of claim 15, wherein the optical signal is a light beam.

19. The method of claim 15, wherein the light beam has a wavelength in a range from about 360 nm to about 410 nm.

20. The method of claim 15, wherein the light beam has with a wavelength in a range from about 400 nm to about 750 nm.

* * * * *

UNITED STATES PATENT AND TRADEMARK OFFICE
CERTIFICATE OF CORRECTION

PATENT NO. : 10,451,564 B2
APPLICATION NO. : 15/962981
DATED : October 22, 2019
INVENTOR(S) : Qin Zhong et al.

Page 1 of 1

It is certified that error appears in the above-identified patent and that said Letters Patent is hereby corrected as shown below:

On the Title Page

In item (73), in Column 1, in "Assignee", Line 2, delete "Clara" and insert -- Clara, CA (US) --, therefor.

In the Specification

In Column 6, Line 43, delete ")(90°" and insert -- (90°) --, therefor.

In the Claims

In Column 8, Line 57, in Claim 20, after "has" delete "with".

Signed and Sealed this
Twenty-fourth Day of December, 2019

Andrei Iancu
*Director of the United States Patent and Trademark Office*